US00PP29960P3

(12) United States Plant Patent
Tupy et al.

(10) Patent No.: US PP29,960 P3
(45) Date of Patent: Dec. 11, 2018

(54) VARIETY OF APPLE TREE NAMED 'UEB 38026'

(50) Latin Name: ***Malus domestica* Borkh.**
Varietal Denomination: UEB 38026

(71) Applicant: Institute of Experimental Botany AS CR, v.v.i. (UEB), Prague (CZ)

(72) Inventors: Jaroslav Tupy, Prague (CZ); Radek Cerny, Ricany u Prahy (CZ); Otto Louda, Pencin u Liberce (CZ); Jan Zima, Turnov (CZ)

(73) Assignee: Institute of Experimental Botany AS CR, v.v.i. (UEB) (CZ)

( * ) Notice: Subject to any disclaimer, the term of this patent is extended or adjusted under 35 U.S.C. 154(b) by 69 days.

(21) Appl. No.: 15/330,707

(22) Filed: Oct. 28, 2016

(65) Prior Publication Data

US 2017/0127584 P1 May 4, 2017

Related U.S. Application Data

(60) Provisional application No. 62/285,464, filed on Oct. 29, 2015.

(51) Int. Cl.
*A01H 5/08* (2018.01)

(52) U.S. Cl.
USPC ..... Plt./161

(58) Field of Classification Search
USPC ..... Plt./161
See application file for complete search history.

*Primary Examiner* — Anne Marie Grunberg
(74) *Attorney, Agent, or Firm* — The Webb Law Firm

(57) ABSTRACT

A new and distinct dessert diploid variety of *Malus domestica* Borkh. that is characterized by very early to early time of harvesting and eating maturity and polygenic resistance against scab. The new variety has a ramified tree type of medium vigor and a spreading tree habit. Fruits are small to medium sized, with a globose-conical shape, yellow ground color, and red overcolor. The fruit flesh has medium firmness, is very juicy, and has a sweet aroma. Bloom, greasiness, and russeting are absent. The variety suits well for organic production as for a home garden.

6 Drawing Sheets

Botanical classification: *Malus domestica* Borkh.
Varietal denomination: 'UEB 38026'.

BACKGROUND OF THE NEW PLANT

The present invention comprises a new and distinct cultivar of apple tree botanically classified as *Malus domestica* Borkh. and known by the varietal name 'UEB 38026'.

The new variety is the result of a cross in a planned breeding program between 'Julia' (female parent, unpatented) and 'Ametyst' (male parent, unpatented). The cross resulting in 'UEB 38026' occurred in the Spring of 1998 in the Czech Republic at 310 meters above sea level with a mean annual temperature of 7.7° C. and a mean annual precipitation of 680 mm. The purpose of the breeding program was to develop an early ripening, dessert apple variety with good eating qualities, attractive appearance, and with polygenic resistance against scab. The new variety was discovered in the summer of 2003 with the first flowers and fruiting on the original seedling in the Czech Republic. Subsequently, the new variety was asexually reproduced in the Czech Republic by budding/grafting on apple rootstocks in the spring of 2006.

The new variety is similar to both parents in early flowering and maturity for consumption time, and in the exhibition of resistance against scab. However, 'UEB 38026' differs from both parents as it has a globose-conical fruit shape, while 'Julia' and 'Ametyst' have a flat globose fruit shape. The fruits of the new variety are small to medium in size when compared to the medium-sized fruits of its parents. Fruits of the new variety have a yellow ground color and red overcolor, while the fruits of 'Julia' have a green ground color and the fruits of 'Ametyst' have a purple-red overcolor.

Further, when compared to apple tree named 'UEB 1813' (concurrently applied for under separate U.S. Plant patent application Ser. No. 15/330,708, the new variety exhibits small to medium-sized, globose-conical shaped fruits, while 'UEB 1813' exhibits medium-sized, globose shaped fruits. Additionally, the fruits of 'UEB 38026' have an earlier ripening time than the fruits of 'UEB 1813'. However, both varieties have a ramified tree type with medium vigor.

The following characteristics also distinguish the new variety from other varieties known to the breeders:

- Early ripening dessert, diploid variety;
- Ramified tree type with medium vigor;
- Spreading tree habit with many fruiting spurs;
- Early bloom timing with a medium blooming period;
- Fruit shape is globose-conical;
- Fruit size is small to medium;
- Fruit ground color is yellow with a medium amount of red overcolor having a pattern that is solidly flush with weakly defined stripes;
- Fruit flesh color is predominantly yellow-orange;
- Flesh is medium firm and very juicy, with a sweet aroma;
- Fruit russet is absent; and
- Resistance against scab on assumed polygenic basis.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type. It should be noted that colors may vary with growing conditions and with time during year.

DESCRIPTION OF THE PLANT

Figure 1:
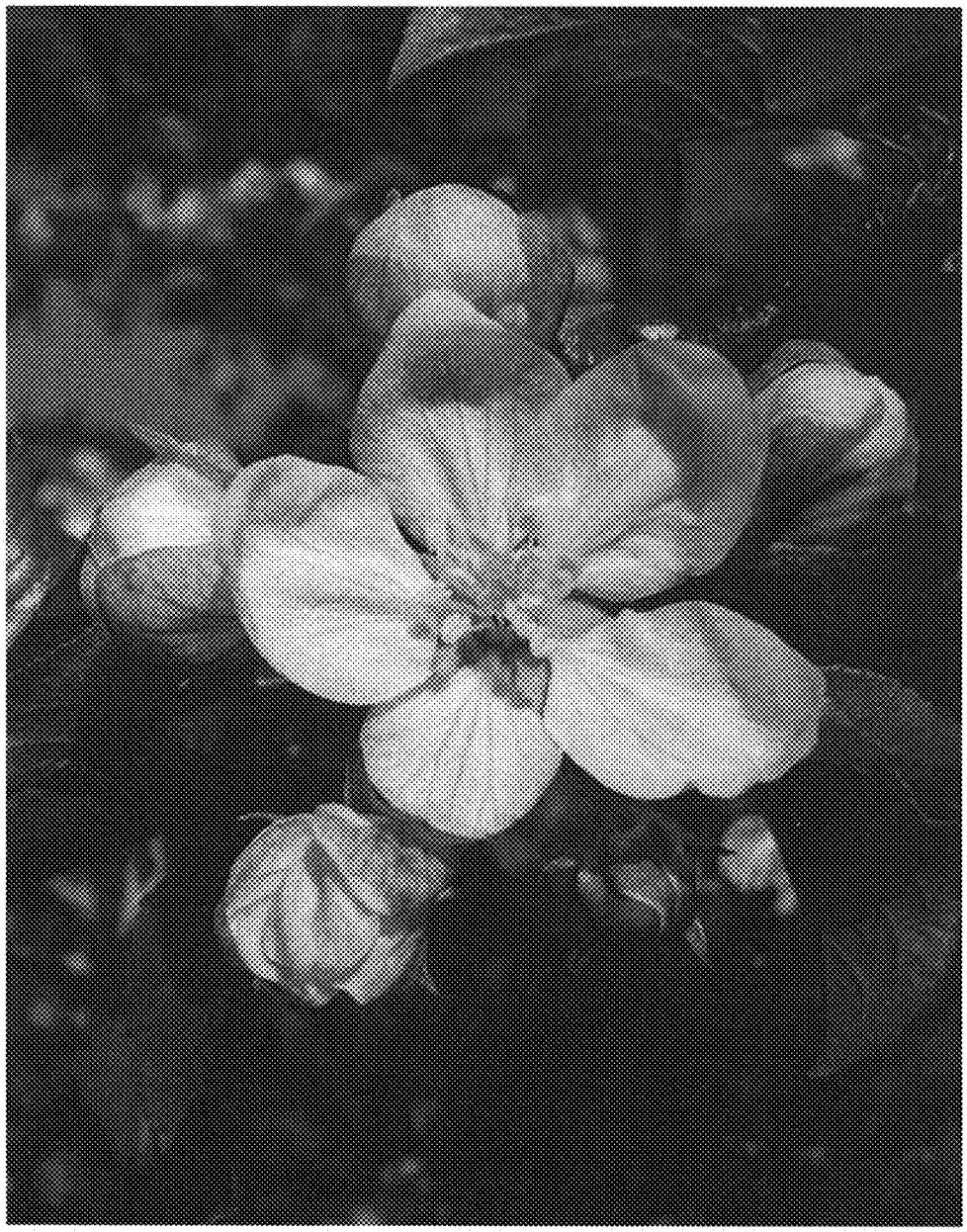
FIG. 1 illustrates a section of a tree of the new variety with opening and fully opened flowers.
Figure 2:
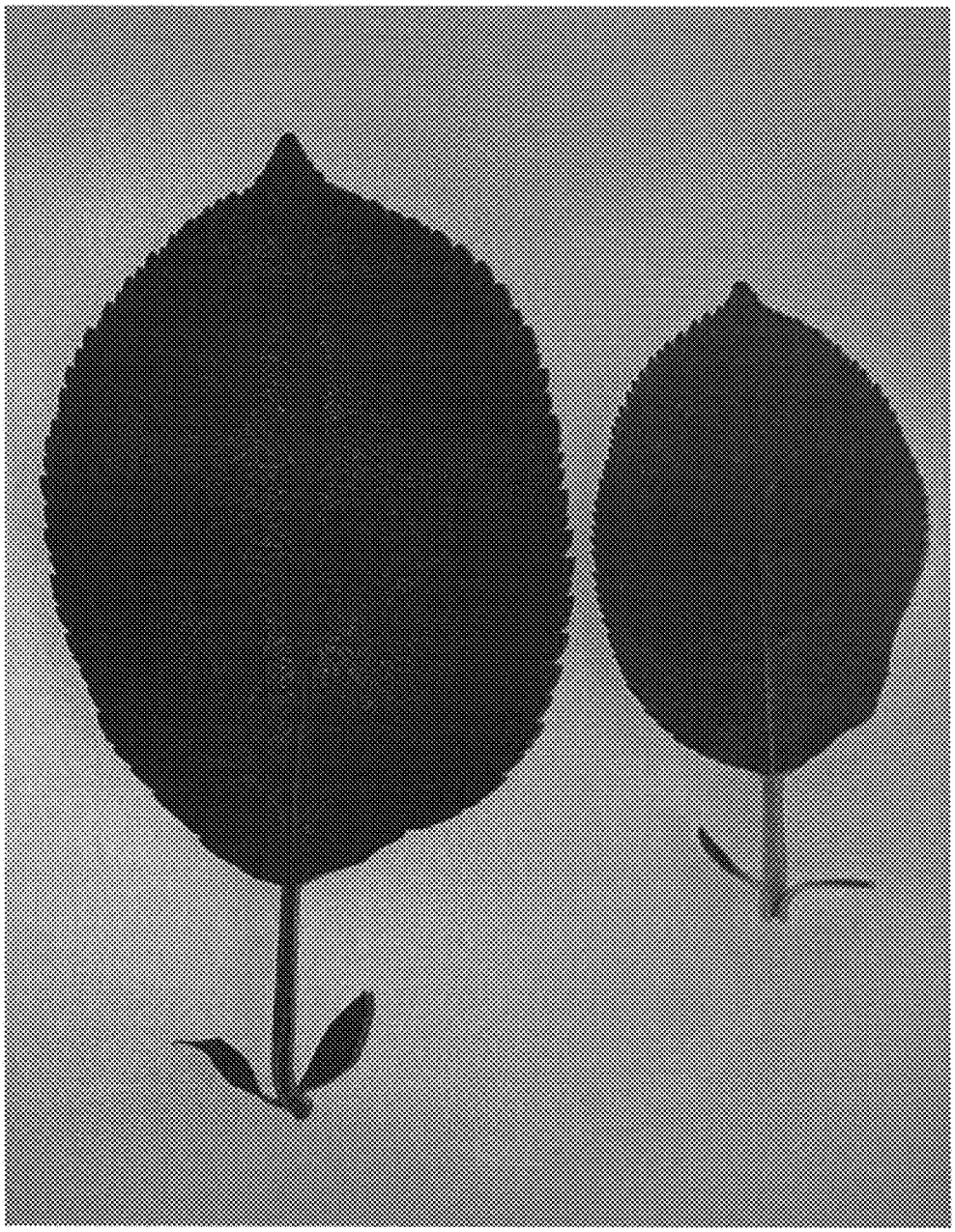
FIG. 2 illustrates a close-up view of a mature leaf and a young leaf of the new variety.
Figure 3:
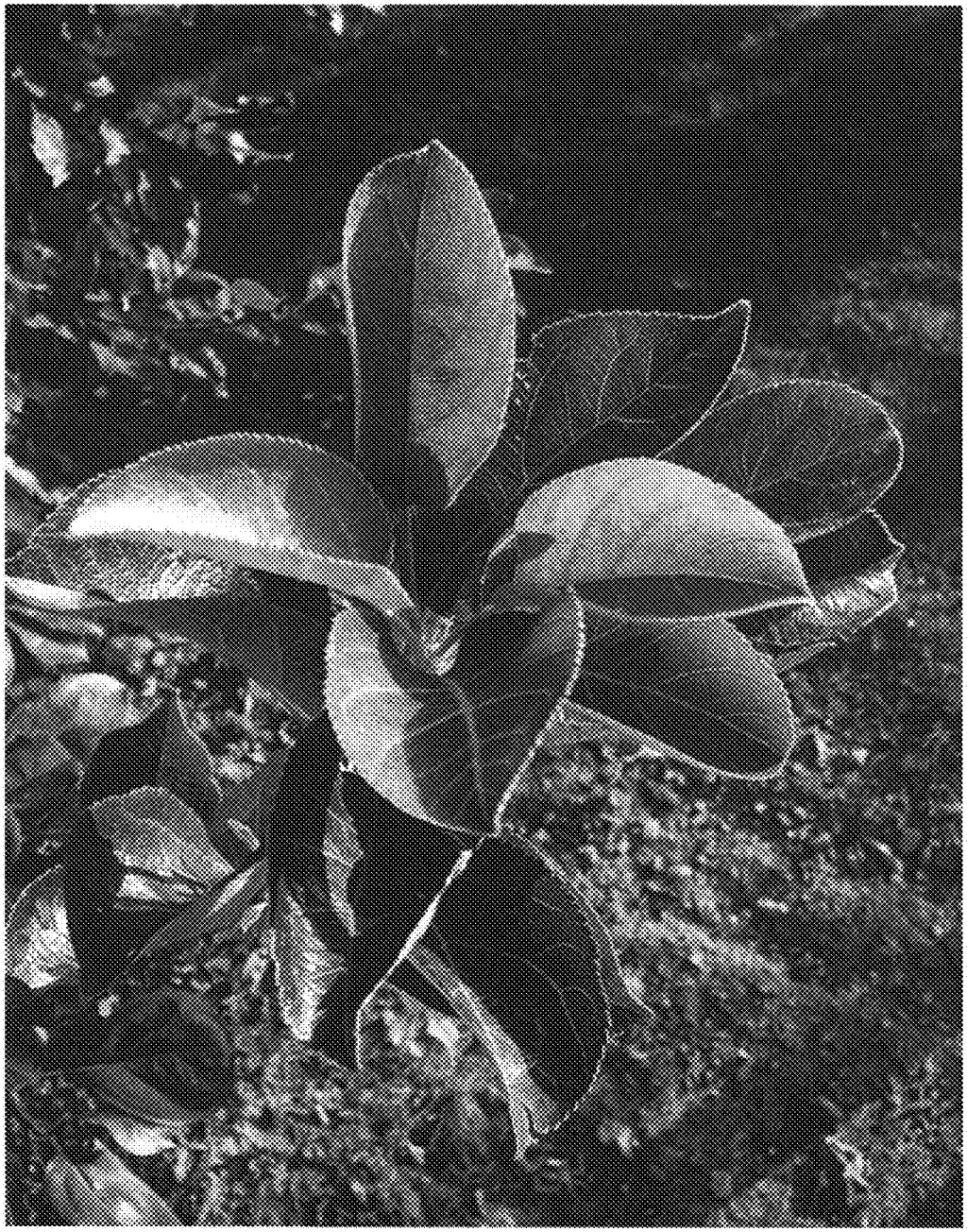
FIG. 3 illustrates a growing shoot of the new variety.
Figure 4:
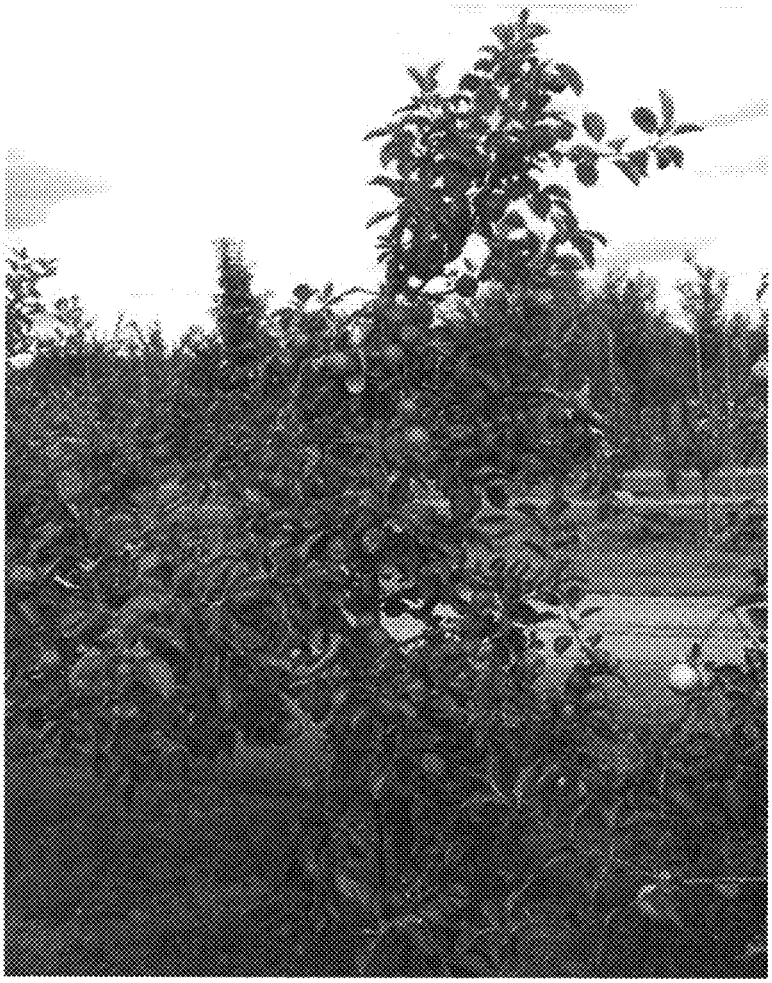
FIG. 4 illustrates a tree of the new variety grafted on MM9 rootstock with fruits at picking maturity.
Figure 5:
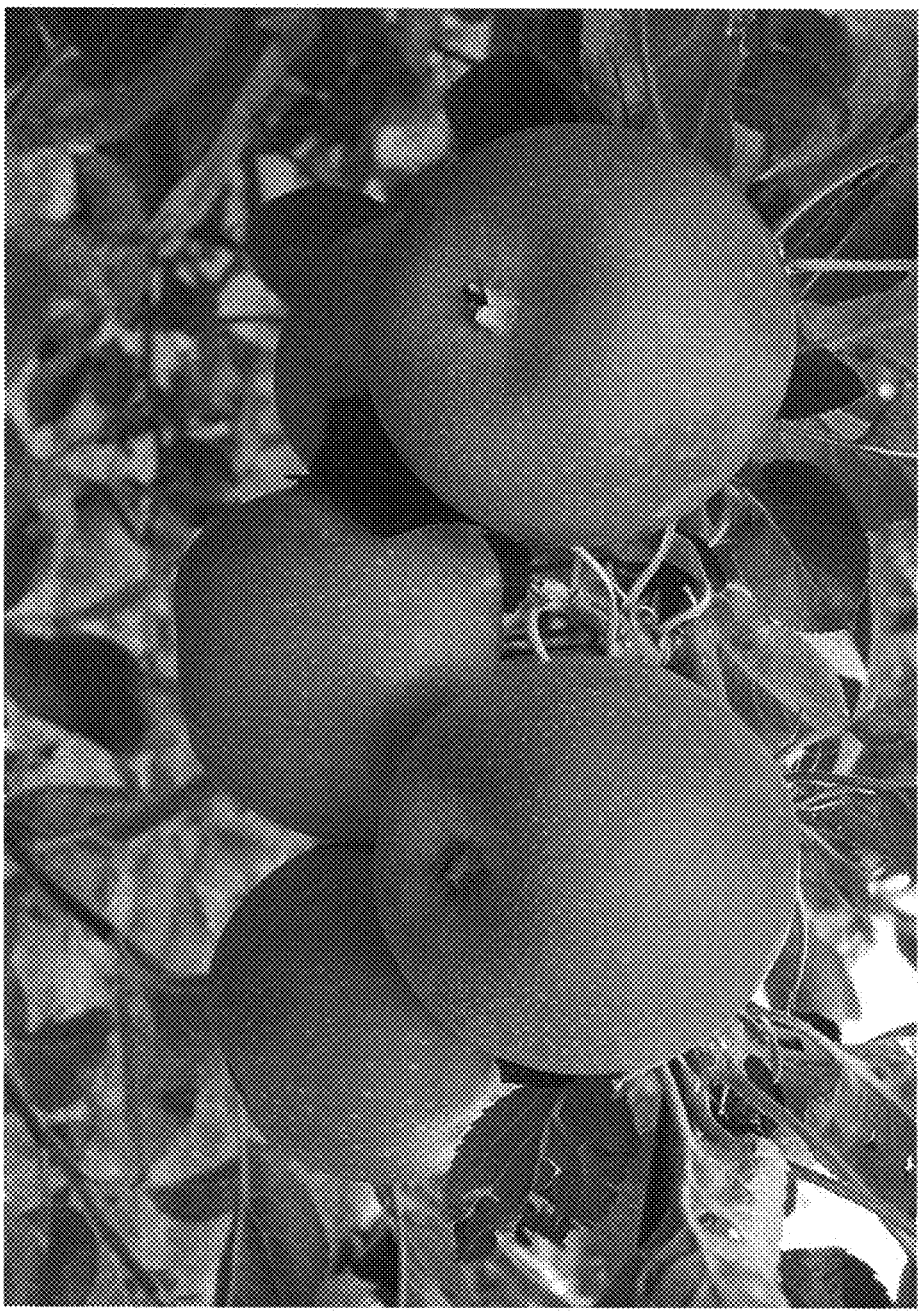
FIG. 5 illustrates a close-up view of the fruits of the new variety at picking maturity.
Figure 6:
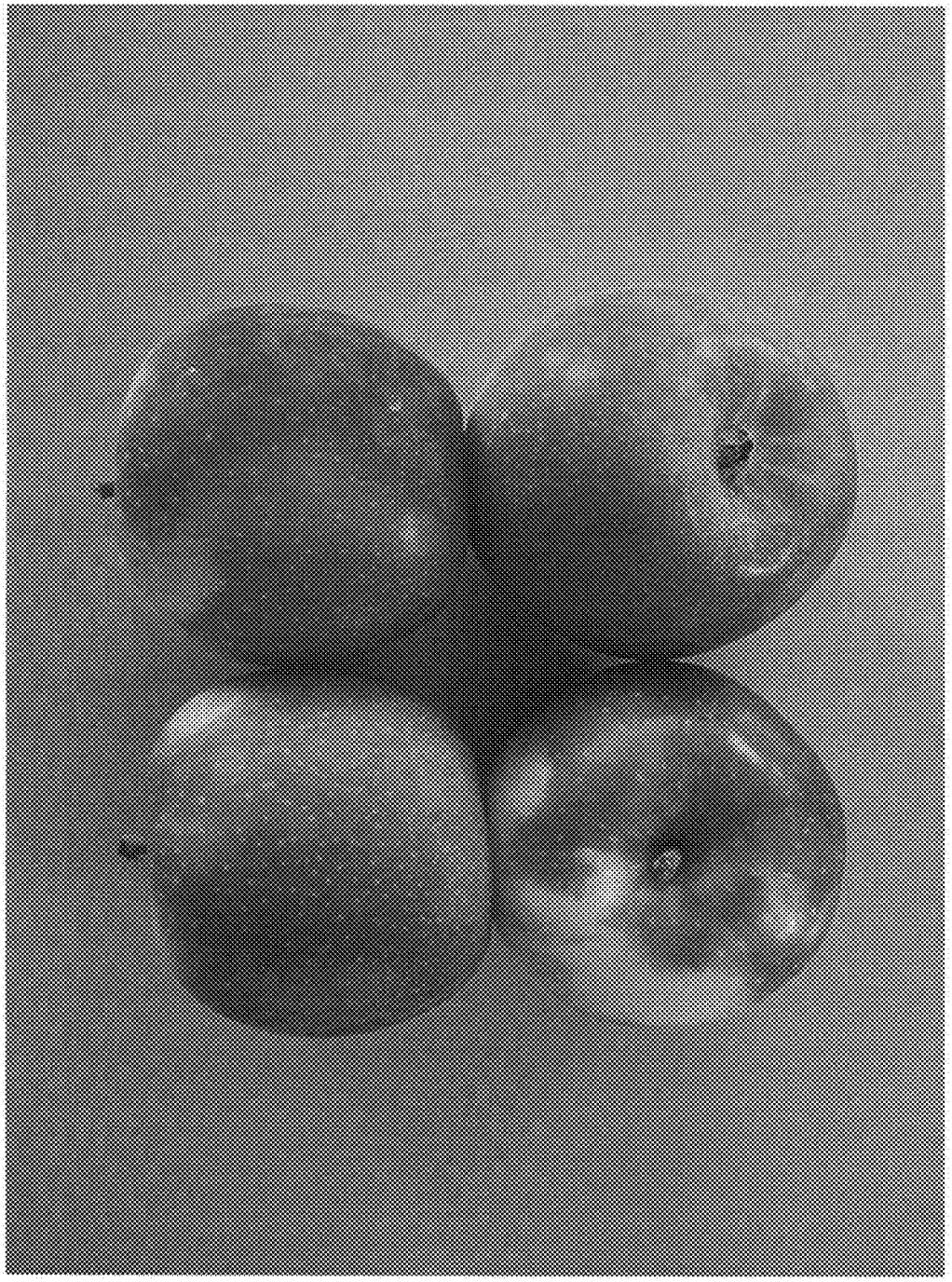
FIG. 6 illustrates details of mature fruits of the new variety.

The following detailed description sets forth characteristics of the new cultivar. The new variety was grown in natural field conditions in the Czech Republic. The following fertilizer combination was used (Kg/ha/year): 55 parts nitrogen, 25 parts phosphorous, 60 parts potassium, 55 parts calcium, and 5 parts magnesium. Color references are primarily according to R.H.S. Colour Chart of The Royal Horticultural Society of London and were identified in natural light.

TREE

Age: 10 years after seedling grafting on MM9 rootstock.
Size: 3.5 m high, 4.0 m wide.
Vigor: Moderate.
Density: Medium open.
Form: Spreading.
Production: Moderately productive.
Growth type: Spreading with slight weeping habit.
Bearing: Annual, mainly on spurs.
Trunk:
- *Size*.—Approximately 17.0 cm in diameter at 30.0 cm from the soil line.
- *Surface texture*.—Smooth to becoming slightly rough.
- *Bark color*.—Greyed-Green Group RHS 197A to 197B.
- *Lenticels* (*at* 100.0 *cm above ground*).—Length: 1.0 mm to 4.0 mm. Width: 0.5 mm to 1.0 mm. Color: Greyed-Orange Group RHS 167B. Density: Variable, about 8 lenticels per 1 $cm^2$.

Branches:
- *Diameter*.—Main branches on the trunk, 5.0 to 8.0 cm.
- *Surface texture*.—Smooth, becoming slightly rough as tree wood matures.
- *Color*.—Greyed-Green Group RHS 197B.
- *Form*.—Straight.
- *Average crotch angle*.—About 70 degrees.
- *Bud arrangement*.—Alternate, with internode lengths at intervals from 1.8 cm to 2.6 cm.
- *Lenticels* (*on a* 1-*year old shoot*).—Length: Typically 1.0 mm to 2.0 mm. Width: Typically 0.5 mm. Shape: Oval. Density: Variable, with about 7 lenticels per 1 $cm^2$. Color: Greyed-Orange Group RHS 167B.

Leaves (measured at the middle of growing shoot):
- *Length*.—About 78.0 mm to about 93.0 mm, averaging 87.0 mm.
- *Width*.—About 49.0 mm to about 79.0 mm, averaging about 63.0 mm.
- *Form*.—Oval.
- *Texture*.—Smooth.
- *Thickness*.—Medium.
- *Base*.—Predominantly symmetric.
- *Apex*.—Acute to acuminate.
- *Margin*.—Serrate.
- *Attitude of leaf blade in relation to the shoot*.—Outwards.
- *Pubescence*.—Upper surface: None present. Lower surface: Very fine.
- *Color*.—Young leaves: Upper surface: Yellow-Green Group 144A. Lower surface: Greyed-Purple Group 187B. Mature leaves: Upper surface: Green Group RHS 139A. Lower surface: Yellow-Green Group RHS 146B.
- *Petiole*.—Shape: Straight, with thickening and flattening at the base. Length: About 24.0 mm to about 34.0 mm, averaging about 28.0 mm. Diameter: About 2.0 mm in the middle. Color: Yellow-Green Group RHS 146C with some Red Group RHS 53A.
- *Veins*.—Venation type: Net-like, medium dense. Color: Upper surface: Yellow-Green Group RHS 144C. Lower surface: Yellow-Green Group RHS 144D.

Flower buds:
- *Pedicel*.—Length: Typically in the range of 20.0-28.0 mm, with an average of 24.0 mm. Diameter: 1.8 mm on average. Color: Predominantly Yellow-Green Group 144B.
- *Bud*.—Length: 17.0 mm on average. Width: 12.0 mm on average. Color: Red-Purple Group RHS 62B to 63C.

Flowers:
- *Bloom timing*.—Early; at the end of April/first of May — about 3 days before 'Golden Delicious'.
- *Blooming period*.—Medium.
- *Pollination requirements*.—Self-sterile, needs pollinators.
- *Number of flowers per cluster*.—5 to 6.
- *Fragrance*.—Mild.
- *Average diameter*.—4.5 cm.
- *Petals*.—Number: 5. Length: From 25.0 to 31.0 mm, with an average of 29.0 mm. Width: From 17.0 to 21.0 mm, with an average of 19.0 mm. Shape: Oval. Apex: Obtuse. Base: Mucronate. Aspect: Positioned overlapping. Margin: Entire. Texture and appearance: Soft and smooth. Color: When opening: Upper surface: Red-Purple Group RHS 63C and partly White Group RHS 155C. Lower surface: Red-Purple Group RHS 65C to 65D and partly White Group RHS 155C. Fully opened: Upper surface: Predominantly White Group RHS 155C and partly Red-Purple Group RHS 65B to 65C. Lower surface: Predominantly White Group RHS 155C and partly Red-Purple Group RHS 65B.
- *Sepals*.—Shape: Long-conical; pointed. Margin: Entire. Texture: Finely pubescent. Length: 10.0 mm to 12.0 mm from the union. Width: 4.0 mm in the middle. Color: Upper surface: Yellow-Green Group RHS 144A. Lower surface: Yellow-Green Group RHS 144B.
- *Stamens*.—Number (per flower): 20. Filament length: 9.0-13.0 mm.
- *Anthers*.—Shape: Oval. Length: 2.0 mm. Color: Yellow Group RHS 10B.
- *Pollen*.—Color: Yellow Group RHS 7B. Amount (generally): Medium to high.

*Pistils*.—Length: 13.0 mm on average.
*Style*.—Length: 8.0 mm on average. Color: Yellow-Green Group RHS 150B.
*Stigma*.—Shape: Rounded. Color: Yellow-Green Group RHS 151B.

Fruit:
*Bearing*.—On spurs and long shoots.
*Maturity when described*.—Eating maturity — after 10 days in common storage.
*Date of picking*.—Aug. 5, 2012.
*Size*.—Axial diameter: Average of 60.5 mm. Transverse diameter: Average of 68.3 mm.
*Form*.—Round-conical.
*Cavity*.—Shape: Funnel. Depth: 11.4 mm on average. Breadth: 25.5 mm on average.
*Basin*.—Shape: Saucer-shaped, slightly ribbed. Depth: 6.3 mm on average. Width: 24.4 mm on average.
*Calyx*.—Persistent with erect lobes, open.

Skin:
*Thickness*.—Medium.
*Texture*.—Smooth, free of russet.
*Tendency to crack*.—Absent.
*Color*.—Red Group RHS 47B to 53A.
*Ground color*.—Yellow Group RHS 4B.
*Extent of young fruit anthocyanin overcolor*.—About 50% — lower intensity of overcolor.
*Percentage of fruit overcolor*.—60-90%.
*Lenticels*.—Average number per fruit: 680. Average length: 0.63 mm. Average width: 0.55 mm. Color: Yellow-White Group RHS 158B.

Flesh:
*Aroma*.—Medium.
*Color*.—Yellow-Orange Group RHS 20D.
*Texture*.—Fine, crisp, and juicy.
*Eating quality*.—Very good, rather sweet, and well-balanced sugar to acid ratio.

Core:
*Bundle area*.—On longitudinal section — onion-shaped, with a height of 26.0 mm and a width of width 35.0 mm.
*Aperture of the locules in the transverse section*.—Moderately open.
*Bundle*.—Number of bunds is 10, with a color of Yellow-Orange Group RHS 22A.
*Calyx tube*.—Funnel-shaped.
*Depth of tube to shoulder*.—16.0 mm.
*Styles*.—Persistent as dry residues.
*Stamens*.—Persistent as dry residues.
*Seed cells*.—Wall: Smooth. Depth: 9.0 mm. Breadth: 4.0 mm on cross section. Longitudinal section: About 21.0 mm (length of seed cell).

Seeds:
*Number perfect*.—8.
*Number in one cell*.—1 to 2.
*Length*.—About 8.0 mm.
*Breadth*.—About 5.0 mm.
*Form*.—Conical to long conical with an acute tip.
*Color*.—Greyed-Orange Group RHS 175 B.

Stem:
*Length*.—10.6 mm on average.
*Width*.—About 3.5 mm.
*Color*.—Yellow-Green Group RHS 151A.

Use: As an early ripening dessert variety.
Shipping quality: Not tested.
Keeping quality: Lasts in natural storage until September.
Tree winter hardiness: No frost damage observed at the place of origin, lowest winter temperatures approximately −20° C.
Bud winter hardiness: No frost damage observed at the place of origin, lowest winter temperatures approximately −20° C.
Drought tolerance: Unknown.
Disease resistance: Resistance on assumed polygenic basis against scab and is mildew tolerant.
Sensitivity: No sensitivity observed to insects, mites, viruses, or diseases to date.

We claim:

1. A new and distinct variety of *Malus domestica* (Borkh.) apple tree plant substantially as is herein described and illustrated.

* * * * *